United States Patent [19]

Knowlton

[11] Patent Number: 5,671,046
[45] Date of Patent: Sep. 23, 1997

[54] DEVICE AND METHOD FOR OPTICALLY DETECTING PARTICLES IN A FREE LIQUID STREAM

[75] Inventor: Dennis J. Knowlton, Boulder, Colo.

[73] Assignee: Particle Measuring Systems, Inc., Boulder, Colo.

[21] Appl. No.: 674,148

[22] Filed: Jul. 1, 1996

[51] Int. Cl.[6] .................................................. G01N 21/00
[52] U.S. Cl. .......................... 356/338; 356/336; 356/339
[58] Field of Search ................................... 356/336, 102, 356/103, 104, 208, 181, 39, 338, 339, 340, 341.342, 343, 73, 318, 364, 40, 41, 42; 250/574, 573, 575, 461.2, 461.1, 239; 350/394; 435/29

[56] References Cited

U.S. PATENT DOCUMENTS

| | | | |
|---|---|---|---|
| 3,758,787 | 9/1973 | Sigrist | 250/574 |
| 3,766,489 | 10/1973 | Rosenberg et al. | 331/94.5 |
| 3,960,449 | 6/1976 | Carleton et al. | 356/103 |
| 4,110,043 | 8/1978 | Eisert | 356/102 |
| 4,281,924 | 8/1981 | Aver et al. | 356/73 |
| 4,498,766 | 2/1985 | Unterleitner | 356/73 |
| 4,522,494 | 6/1985 | Bonner | 356/39 |
| 4,609,286 | 9/1986 | Sage, Jr. | 356/73 |
| 4,662,742 | 5/1987 | Chupp | 356/39 |
| 4,728,190 | 3/1988 | Knollenberg | 356/336 |
| 4,752,131 | 6/1988 | Eisenlaven et al. | 356/338 |
| 4,781,459 | 11/1988 | Suzuki | 356/335 |
| 4,798,465 | 1/1989 | Knollenberg | 356/336 |
| 4,850,707 | 7/1989 | Bowen et al. | 356/336 |
| 4,876,458 | 10/1989 | Takeda et al. | 250/574 |
| 5,067,814 | 11/1991 | Suzuki et al. | 356/339 |
| 5,396,333 | 3/1995 | Aleshin et al. | 356/385 |

OTHER PUBLICATIONS

"The Measurement of Particle Sizes Below 0.1 Micrometers", Knollenberg Journal of Environmental Science, Jan.–Feb. 1985.
"In Situ' Optical Particle Size Measurements In Liquid Media", Knollenberg Proceedings of Pure Water Conference, Palo Alto, California, Jan. 13–14, 1983.

*Primary Examiner*—Frank G. Font
*Assistant Examiner*—Michael P. Stafira
*Attorney, Agent, or Firm*—Robert E. Harris

[57] ABSTRACT

Device and method are disclosed for optically detecting particles in a free (i.e., unenclosed) stream of liquid. The free liquid stream is produced by ejecting liquid under pressure from a nozzle so that the stream has a smooth round surface. A laser beam intersects the free liquid stream and light scattered by particles in the free liquid stream is collected and processed to provide an output indicative of size and/or number of particles causing the light to be scattered. The free liquid stream is preferably directed vertically downward, and the laser beam and light collector are angularly positioned with respect to the free liquid stream and one another with the light collector collecting scattered light at the intersection of the light beam and the free liquid stream. Embodiments are also disclosed wherein scattered light is collected at a collecting position spaced along the free liquid stream from an illuminating position where the laser beam intersects the free liquid stream with the scattered light traveling along the liquid free stream between the illuminating and collecting positions.

32 Claims, 2 Drawing Sheets

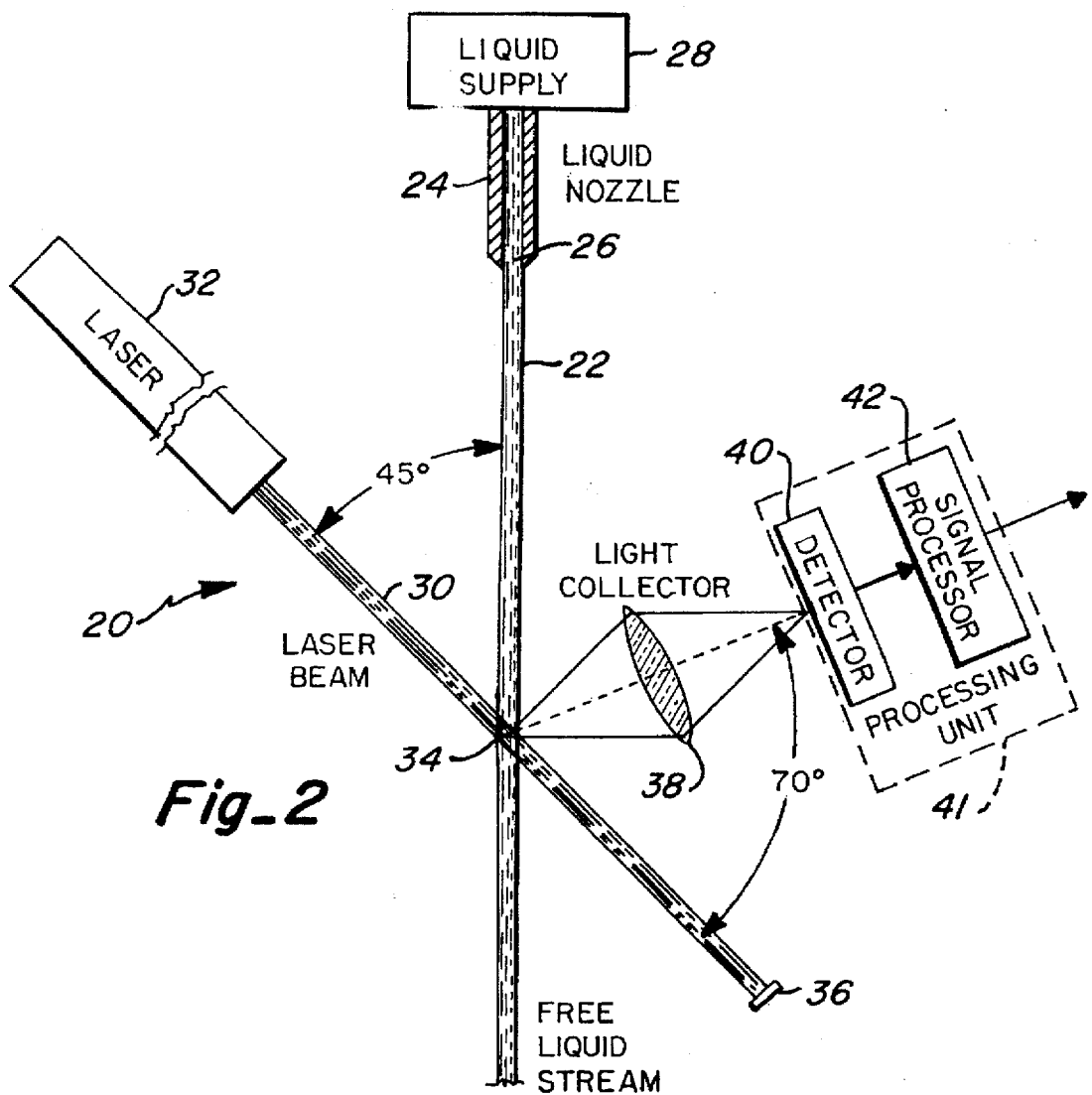
Fig_2
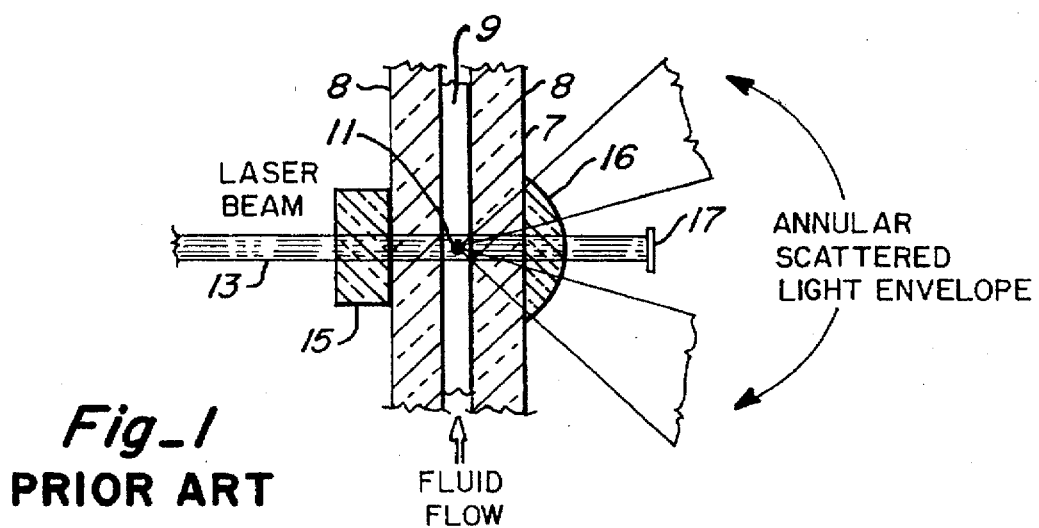
Fig_1
PRIOR ART

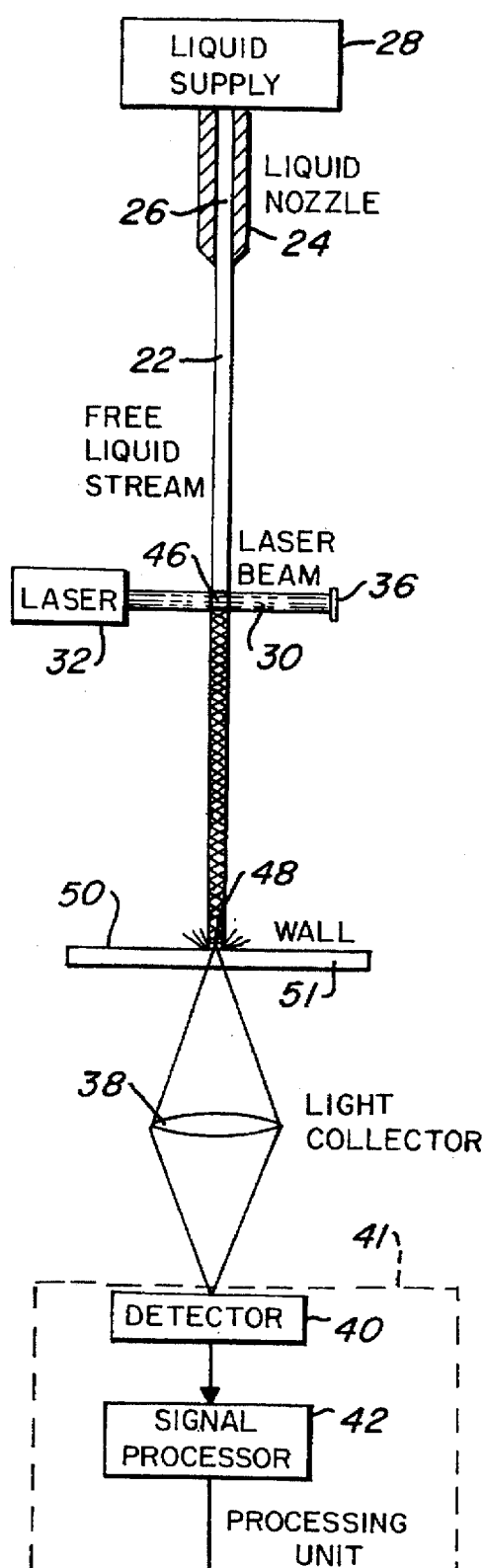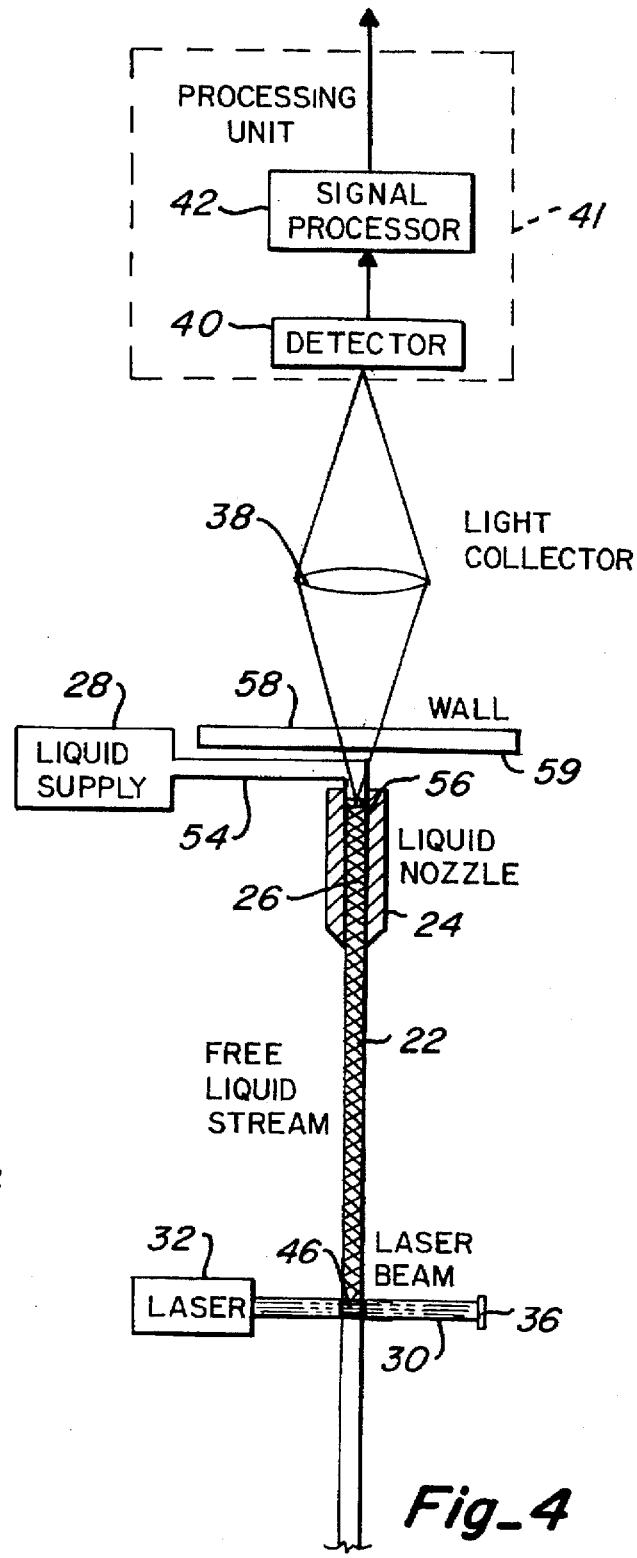

DEVICE AND METHOD FOR OPTICALLY DETECTING PARTICLES IN A FREE LIQUID STREAM

FIELD OF THE INVENTION

This invention relates to particle detection, and, more particularly, relates to optical detection of particles in a free stream of liquid.

BACKGROUND OF THE INVENTION

The detection of particles in a fluid, including detection of the particles to determine parameters such as size and/or number, has become increasingly important over the past few years, and devices and methods have heretofore been suggested and/or utilized for achieving such detection.

Particle detection using lasers to illuminate a sensing region to cause particles at the sensing region to scatter light has also heretofore been suggested and/or utilized, and such devices are known to detect particles in a gas, such as air, at least as small as 0.1 microns (see, for example, U.S. Pat. No. 4,798,465 to Knollenberg, and an article by R. G. Knollenberg entitled "The Measurement of Particle Sizes Below 0.1 Micrometers", Journal of Environmental Science, Jan–Feb. 1985).

The detection of particles in a liquid has also been heretofore suggested and/or utilized, and such detection has also become increasingly important over the past few years, particularly, for example, in the semiconductor and related electronic component industries where liquid contamination cannot be tolerated.

Devices that are currently used to monitor contaminates in liquids, such as process liquids, are largely optical using light scattering to size particles, and these devices are either in-situ type devices that measure remotely and sample only a small portion of the total volume utilized, or are volumetric type devices that sample substantially all of the total volume utilized.

A device of the volumetric type usually has a restricted passage to ensure that all of the fluid passes through the monitoring, or sensing, region (unlike that of the in-situ type device which usually has no restricted passage at the sensing region since only a portion of the total volume is sampled), and volumetric type devices have heretofore required some kind of fluid confining walls that have been sources of stray light. Such stray light establishes a noise background level from which light scattered by particles must be distinguished, or differentiated. If the noise background is as great, or greater than, the particle scattering signal, the particles cannot be detected.

An arrangement for minimizing background noise due to stray light produced, at least in part, by a capillary confining the liquid at a sensing region is shown in U.S. Pat. No. 4,728,190 to Knollenberg.

In addition, an arrangement has also heretofore been suggested for detecting particles in a liquid wherein a liquid stream is injected upwardly into a cell that is filled with liquid (see U.S. Pat. No. 5,067,814 to Suzuki et el.), and a free stream of liquid has heretofore been suggested in connection with a device wherein detection and/or sizing of particles is not achieved by the device (see, for example, U.S. Pat. Nos. 3,766,489 to Rosenberg et al. and 4,281,924 to Auer et al.).

SUMMARY OF THE INVENTION

This invention provides device and method for optically detecting particles, including detecting to determine parameters of the particles such as size and/or number, in a free (i.e., unenclosed) liquid stream utilizing light scattering, with the device being preferably a volumetric type device that achieves high size resolution.

A free liquid stream, preferably a smooth round free liquid stream and preferably directed vertically downward, is intersected by a light beam, preferably a laser beam, to cause light scattering that is collected by a light collector, with the light beam and the light collector preferably being angularly positioned with respect to the free liquid stream and one another, with the collected scattered light being processed, preferably in a processing unit that includes a detector and a signal processor, to provide an output indicative of at least one of size and number of particles in the free liquid stream causing light scattering.

In one embodiment of this invention, the scattered light is collected at the sensing region defined by the intersection of the light beam and the free liquid stream, while, in alternate embodiments, scattered light is collected at a collecting position spaced along the free liquid stream with respect to the illuminating, or scattering, position where the light beam intersects the free liquid stream with the scattered light flowing along the free liquid stream between the illuminating and collecting positions.

It is therefore an object of this invention to provide device and method for detecting articles in a free liquid stream.

It is another object of this invention to provide device and method for optically detecting particles in a free liquid stream utilizing light scattering.

It is still another object of this invention to provide device and method for optically detecting particles in a free liquid stream that provides high size resolution.

It is still another object of this invention to provide device and method for detecting particles in a free liquid stream having a smooth round liquid stream.

It is still another object of this invention to provide device and method for detecting particles in a free liquid stream wherein the free liquid stream is intersected by a light beam so that particles in the free liquid stream cause light scattering, with a light collector collecting the scattered light for processing to provide an output that is indicative of at least one of size and number of particles in the free liquid stream causing light scattering.

It is still another object of this invention to provide device and method for detecting particles in a free liquid stream wherein a light beam intersects the free liquid stream at a sensing region to scatter particles thereat, and a light collector collects light at the sensing region for processing to provide an output indicative of at least the size of particles causing the light to be scattered at the sensing region.

It is still another object of this invention to provide improved device and method for detecting particles in a free liquid stream wherein the liquid free stream is intersected by a light beam at an illuminating position so that particles in the free liquid stream scatter particles, and a light collector collects scattered light at a collecting position spaced along the free liquid stream from the illuminating position with scattered light traveling along the free liquid stream from the illuminating position to the collecting position.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is simplified partial side view illustrating a known device wherein a capillary is used to confine the liquid at the sensing region;

FIG. 2 is a simplified illustration of the device of this invention for particle detection in a free liquid stream; and FIGS. 3 and 4 are simplified illustrations of alternate embodiments of this invention for particle detection in a free liquid stream.

DESCRIPTION OF THE INVENTION

A known arrangement for detecting particles in a liquid is illustrated in FIG. 1 to include a capillary 7 having transparent walls 8 defining a passage 9 through which liquid is confined and conveyed through sensing, or monitoring, region 11. Laser beam 13 is directed through window 15 to monitoring region 11 with the beam passing through monitoring region 11 and lens 16, adjacent to the monitoring region, being trapped at beam light trap 17.

Light scattered by the particles within passage 9, defined by capillary 7 at monitoring region 11, is passed through lens 16 and collected, with the collected light becoming the signal for particle size analysis, as is well known.

In this invention, apparatus 20 produces and utilizes a free (i.e., unenclosed) stream of liquid 22, as illustrated in FIGS. 2 through 4. By providing a free liquid stream, generation of stray light due to liquid confining walls and the like is eliminated to thereby enhance detection of smaller size particles than would otherwise be possible.

As shown in FIGS. 2 through 4, free liquid stream 22 is provided by a liquid ejector, such as liquid nozzle, 24, preferably of stainless steel, having liquid passage 26 therethrough. Liquid passage 26 has little or no roughness to thereby eliminate optical noise at this interface, and liquid forced through passage 26 from a conventional pressurized liquid supply source 28 is discharged from nozzle 24 in a round stream having a smooth surface to thereby allow detection of quite small particles in the free liquid stream with the detection limit being based almost entirely on liquid bulk scattering.

Laser beam 30 is provided by conventional laser 32, and beam 30 is preferably angularly directed toward and through free liquid stream 22 to illuminate the intersection between the laser beam and the free liquid stream. As shown in the embodiment of the invention as illustrated in FIG. 2, the intersection between laser beam 30 and free liquid stream 22 is sensing, or monitoring region 34, and the laser beam, after passing through sensing region 34, is trapped by beam trap 36.

With total illumination by laser beam 30 of an entire region, such as the entire intersection between the laser beam and the free liquid stream (i.e., the entire sensing region 34, for example, as shown in FIG. 2), the device of this invention is a volumetric type device in which the entire free liquid stream passes through the intersection of the liquid free stream and the laser beam, thus assuring that all particles in the free liquid stream at least as large as the minimum selected, or threshold, size can be detected.

Particles in the free liquid stream passing through sensing region 34 scatter light according to Rayleigh and/or Mie scattering principles when sensing region 34 is illuminated by laser beam 30, as is also known.

The scattered light is collected by light collector, or collecting optics, 38 focused on sensing region 34 (such as by a lens arrangement, as indicated in FIGS. 2 through 4, which lens arrangement preferably has a high numerical aperture (NA) and one or higher magnification), and the collected scattered light is coupled to detector unit 40 (preferably a solid state detector unit) of processing unit 41. Detector 40 provides an electrical pulse signal output that is indicative of scattered light received by the detector unit, and hence this output is directly related to the size of the particles in the free liquid stream causing the light to be scattered. The electrical signal output from detector 40 is coupled to signal processor 42 of processing unit 41, and signal processor 42 provides an output indicative of at least one of particle size and number, which output can be displayed in real time and/or stored for future use.

Laser 32, light collector 38, detector unit 40, and signal processor 42 can be conventional, and can be, for example, elements as shown and described in U.S. Pat. No. 4,728,190 to Knollenberg and/or U.S. Pat. No. 4,798,465 to Knollenberg.

As particularly indicated in FIG. 2, laser beam 30 and light collector 38 are angularly positioned with respect to one another and with respect to vertically downward directed free liquid stream 22 (free liquid stream 22 is preferably directed vertically downward to gain stability with changing flow rates). As shown, laser beam 30 is positioned to intersect free liquid stream 22 at an angle of about forty-five degrees (45°) at sensing region 34, and collecting optics 38 is positioned at an angle of about seventy degrees (70°) with respect to laser beam 30 at sensing region 34 (and hence is positioned at an angle of about sixty-five degrees (65°) with respect to free liquid stream 22 at sensing region 34).

Both laser 32 and light collector 38 are preferably polarized in the vertical plane for maximizing light collecting efficiency, and the relative angular positioning of the laser beam and the collecting optics are selected to keep reflected light from being collected by the light collector.

Alternate embodiments of this invention are shown in FIGS. 3 and 4. In both of these alternate embodiments, a free liquid stream 22 is provided in the same manner as described above in connection with the embodiment of the invention as shown in FIG. 2.

As shown in FIGS. 3 and 4, laser 32 provides a laser beam 30 that normally intersects free liquid stream 22 at a first, or illuminating region, 46. As indicated in FIG. 3, a second, or collecting, region 48 is spaced from illuminating region 46 along free liquid stream 22 with illuminating region 46 being between liquid nozzle 24 and collecting region 48. As also shown in FIG. 3, free liquid stream 22 is directed toward, and comes into contact with, surface 50 of wall 51, and collecting region 48 is located adjacent to wall 51.

As further indicated in FIGS. 3 and 4, free liquid stream 22 acts as a light pipe so that light scattered by particles at illuminating region 46 travels, or passes, along the free liquid stream (although the scattered light travels in both directions away from the illuminating region, the scattered light has been indicated as traveling down the free liquid stream in FIG. 3 and up the free liquid stream in FIG. 4 due to the positioning of the collecting region relative to the illuminating region in FIGS. 3 and 4).

Wall 51 must be capable of passing light therethrough, and may be, for example, a glass sheet. As shown in FIG. 3, light collector 38 is preferably positioned behind wall 51 (i.e., at the side of wall 51 opposite to surface 50) and in line with, but below, the direction of flow of free liquid stream 22. Light collector 38 is focused through wall 51 to collect scattered light traveling down free liquid stream 22 from illuminating region 46 to collecting region 48, and scattered light collected by light collector 38 through wall 51 is directed to detector 40 for detection and subsequent processing by signal processor 42 in the same manner as described above in connection with the embodiment of the invention as shown in FIG. 2.

As shown in FIG. 4, liquid supply 28 is connected with passage 26 in liquid nozzle 24 through pipe 54 extending normally from the top of passage 26. In this embodiment, collecting region 56 is positioned at the top portion of liquid nozzle 24, and wall 58 (capable of passing light, such as, for example, a glass sheet), is positioned above flow nozzle 24 with surface 59 of wall 58 being adjacent to the top portion of liquid nozzle 24.

Light collector 38 is positioned behind wall 58 (i.e., at the side of wall 58 opposite to surface 59), and in line with, but above, the direction of flow of free liquid stream 22. Light collector 22 is focused through wall 58 to collect scattered light traveling up free liquid stream 22 from illuminating region 46 to collecting region 56, and scattered light collected by collecting optics 38 through wall 58 is detected and then processed in the same manner as described above with respect to the embodiments of the invention as shown in FIGS. 2 and 3.

Using a light nozzle providing a 0.012 inch (0.012") diameter free liquid stream having a flow rate of 10 milliliters per minute (10 ml/min) and illuminated by a laser beam twenty microns (20 μm) wide at the intersection of the laser beam with the liquid free stream, particles having a size of 0.1 microns and lower have been detected according to this invention.

It is meant to be realized from the foregoing that this invention is not meant to be limited to the exact configurations and/or relative angular positioning of elements as shown in the various embodiments set forth herein, and various modifications, as would be obvious to one skilled in the art, including, for example, orienting free liquid stream 22 other than vertically downward and/or using different angular relationships between the laser beam, the free liquid stream, and/or the light collector so long as the efficiency of particle sizing is not adversely affected.

As can be appreciated from the foregoing, this invention provides device and method for efficiently detecting particles in a free liquid stream.

What is claimed is:

1. A device for optically detecting particles in a free liquid stream, said device comprising:

a liquid ejector for providing a free liquid stream capable of having particles therein, said free liquid stream having predetermined first and second regions that are spaced from one another along said free liquid stream;

a light source for providing a light beam that intersects said free liquid stream at said first region so that particles in said free liquid stream at said first region cause scattering of light that travels along said free liquid stream from said first region to said second region;

a light collector for collecting light at said second region that has been scattered by particles in said free liquid stream at said first region; and a processing unit for receiving said scattered light collected by said light collector and, responsive thereto, providing an output that is indicative of at least one of size and number of said particles in said free liquid stream causing said light scattering at said first region.

2. The device of claim 1 wherein said light beam angularly intersects said free liquid stream at said first region, and wherein said light collector collects light at said second region from substantially the entirety of said intersection of said light beam and said free liquid stream whereby said device operates as a volumetric type device.

3. The device of claim 1 wherein said light source is a laser providing a laser beam as said light beam that intersects said free liquid stream at said first region.

4. The device of claim 1 wherein said free liquid stream is a smooth round stream.

5. The device of claim 1 wherein said liquid ejector includes a liquid nozzle for receiving liquid under pressure to provide said free liquid stream.

6. The device of claim 1 wherein said free liquid stream is directed substantially vertically downward.

7. The device of claim 1 wherein said processing unit includes a detector for providing an electrical signal output based upon said scattered light received by said detector from said light collector, and a signal processor for receiving said electrical signal output from said detector and, responsive thereto, providing said output indicative of at least one of size and number of said particles in said free liquid stream causing said light scattering.

8. The device of claim 1 wherein said device provides an output indicative of particle size with said output having high resolution.

9. The device of claim 8 wherein said output indicative of particle size provides an output indicative of particles at least as small as 0.1 microns.

10. A device for optically detecting particles in a free liquid stream, said device comprising:

a liquid nozzle for providing a smooth free liquid stream capable of having particles therein;

a laser for providing a laser beam that intersects said liquid free stream at a sensing region so that particles in said free liquid stream cause scattering of light at said sensing region;

a light collector for collecting said scattered light at said sensing region, said light collector being positioned to collect scattered light at an angle of about 65° with respect to said free liquid stream;

a detector for receiving light collected by said light collector and providing an electrical signal output indicative thereof; and a signal processor for receiving said electrical signal output from said detector and responsive thereto providing an output indicative of at least one of size and number of particles causing said light scattering at said sensing region.

11. The device of claim 10 wherein said liquid nozzle directs said free liquid stream substantially vertically downward.

12. The device of claim 10, wherein said laser beam intersects said free liquid stream at an angle of about 45° with respect to said free liquid stream.

13. The device of claim 10 wherein said laser beam intersects said free liquid stream at an angle of about 45° with respect to said free liquid stream, and wherein said light collector is positioned to collect scattered light at an angle of about 70° with respect to said laser beam.

14. The device of claim 10 wherein said light collector includes a lens arrangement focused onto said sensing region to thereby collect scattered light at said sensing region.

15. A device for optically detecting particles in a free liquid stream, said device comprising:
   a liquid nozzle for providing a smooth free liquid stream capable of having particles therein, said free liquid stream having predetermined first and second regions that are spaced from one another along said free liquid stream;
   a wall having a surface in the path of said free liquid stream so that said free liquid stream contacts said surface of said wall, and wherein said second region is adjacent to said surface of said wall;
   a laser for providing a laser beam that intersects said free liquid stream at said first region such that particles in said free liquid stream at said first region cause light scattering that travels along said liquid free stream from said first region to said second region;
   a light collector for collecting scattered light at said second region; and
   a processing unit for receiving said scattered light collected by said light collector and, responsive thereto, providing an output indicative of at least one of size and number of particles causing said light scattering at said first region.

16. The device of claim 15 wherein said liquid nozzle directs said free liquid stream substantially vertically downward.

17. The device of claim 15 wherein said laser beam substantially normally intersects said free liquid stream.

18. The device of claim 15 wherein said first region is between said liquid nozzle and said second region, and wherein scattered light travels along said free liquid stream from said first region to said second region in a direction away from said liquid nozzle.

19. The device of claim 15 wherein said wall is capable of passing light therethrough, and wherein said light collector is positioned at the side of said wall opposite to that of said second region whereby scattered light received by said light collector passes through said wall.

20. The device of claim 15 wherein said second region is at said liquid nozzle, and wherein said scattered light travels along said free liquid stream from said first region to said second region in a direction toward said liquid nozzle.

21. The device of claim 20 wherein said wall is positioned adjacent to said liquid nozzle and capable of passing light therethrough, and wherein said light collector is positioned at the side of said wall opposite to that of said liquid nozzle whereby scattered light received by said light collector passes through said wall.

22. A method for optically detecting particles in a free liquid stream, said method comprising:
   providing a free liquid stream capable of having particles therein, said free liquid stream having predetermined first and second regions that are spaced from one another along said free liquid stream;
   directing light to intersect said free liquid stream at said first region so that particles in the free liquid stream at said first region scatter light that travels along said free liquid stream from said first region to said second region;
   collecting light at said second region that is scattered by particles in the free liquid stream at said first region; and
   providing an output based upon the collected light scattered by the particles in the free liquid stream at said first region with said output being an output indicative of at least one of size and number of said particles.

23. The method of claim 22 wherein said method includes providing volumetric operation by causing said light to angularly intersect said free liquid stream at said first region and causing said light to be collected at said second region from substantially the entirety of the intersection of said light beam and said free liquid stream.

24. The method of claim 22 wherein said step of providing said free liquid stream includes providing a smooth round free liquid stream, and wherein said step of directing light to intersect said free liquid stream at said first region includes providing a laser beam as said light beam intersecting said smooth round free liquid stream at said first region.

25. The method of claim 22 wherein said step of providing said free liquid stream includes directing said free liquid stream substantially vertically downward, and wherein said step of directing light to intersect said free liquid stream at said first region includes causing said light to angularly intersect said free liquid stream at said first region.

26. The method of claim 22 wherein said step of proving an output includes collecting the scattered light at said second region to provide an electrical signal output indicative thereof, and processing the electrical signal output to provide said output indicative of at least one of size and number of said particles scattered at said first region.

27. The method of claim 22 wherein said method includes detecting particles at least as small as 0.1 microns.

28. The device of claim 1 wherein said first region is between said liquid nozzle and said second region, and wherein said scattered light travels along said free liquid stream from said first region to said second region in a direction away from said liquid nozzle.

29. The device of claim 28 wherein said device also includes a wall having a surface in the path of said free liquid stream so that said free liquid stream contacts said surface of said wall, and wherein said second region is adjacent to said surface of said wall.

30. The device of claim 29 wherein said wall is capable of passing light therethrough, and wherein said light collector is positioned at the side of said wall opposite to that of said second region whereby scattered light received by said light collector passes through said wall.

31. The device of claim 1 wherein said second region is at said liquid nozzle, and wherein said scattered light travels along said free liquid stream from said first region to said second region in a direction toward said liquid nozzle.

32. The device of claim 31 wherein said device also includes a wall positioned adjacent to said liquid nozzle and capable of passing light therethrough, and wherein said light collector is positioned at the side of said wall opposite to that of said liquid nozzle whereby scattered light received by said light collector passes through said wall.

* * * * *